United States Patent
Kupper

(10) Patent No.: US 10,624,859 B2
(45) Date of Patent: Apr. 21, 2020

(54) SYSTEMS AND METHODS FOR INCREASING STABILITY OF DRONABINOL COMPOSITIONS

(71) Applicant: Rhodes Technologies, Coventry, RI (US)

(72) Inventor: Robert J. Kupper, Warwick, RI (US)

(73) Assignee: Rhodes Technologies, Coventry, RI (US)

(*) Notice: Subject to any disclaimer, the term of this patent is extended or adjusted under 35 U.S.C. 154(b) by 132 days.

(21) Appl. No.: 14/416,202

(22) PCT Filed: Aug. 20, 2013

(86) PCT No.: PCT/IB2013/001825
§ 371 (c)(1),
(2) Date: Jan. 21, 2015

(87) PCT Pub. No.: WO2014/030053
PCT Pub. Date: Feb. 27, 2014

(65) Prior Publication Data
US 2015/0238428 A1    Aug. 27, 2015

Related U.S. Application Data

(60) Provisional application No. 61/691,073, filed on Aug. 20, 2012.

(51) Int. Cl.
*A61K 9/48* (2006.01)
*C07D 311/80* (2006.01)
*A61K 31/352* (2006.01)
*A61K 31/353* (2006.01)

(52) U.S. Cl.
CPC .............. *A61K 9/48* (2013.01); *A61K 31/352* (2013.01); *A61K 31/353* (2013.01); *C07D 311/80* (2013.01)

(58) Field of Classification Search
USPC ........................................................ 424/456
See application file for complete search history.

(56) References Cited

U.S. PATENT DOCUMENTS

| | | | |
|---|---|---|---|
| 2003/0229027 A1* | 12/2003 | Eissens | A61K 9/1652 514/23 |
| 2006/0160888 A1* | 7/2006 | Kottayil | A61K 9/4875 514/454 |
| 2009/0169629 A1 | 7/2009 | Lambert et al. | |

FOREIGN PATENT DOCUMENTS

| WO | 2006053766 | 5/2006 |
|---|---|---|
| WO | 2011146876 | 11/2011 |

OTHER PUBLICATIONS

Vaczek (Pharmaceutical & Medical Packaging News, Jul. 2006, vol. 14, No. 7; http://www.pmpnews.com/print/article/modeling-moisture-control).*
Who (http://www.whoint/medicines/areas/quality_safety/4.2DronabinolCritReview.pdf; accessed Nov. 13, 2017).*
Multisorb (https://news.thomasnet.com/fullstory/canisters-elirninate-oxygen-for-drug-product-stability-517400; Apr. 24, 2007).*
StabilOx1 (StabilOx product brochure provided by Applicant, dated 2016).*
StabilOx2 (https://www.pharmaceuticalonline.com/doc/stabilox-system-0001, 2009).*

* cited by examiner

*Primary Examiner* — Devang K Thakor
(74) *Attorney, Agent, or Firm* — Lowenstein Sandler LLP

(57) ABSTRACT

Disclosed in certain embodiments is a system and method of providing a dronabinol oral solid dosage form with increased stability.

18 Claims, No Drawings

SYSTEMS AND METHODS FOR INCREASING STABILITY OF DRONABINOL COMPOSITIONS

FIELD OF THE INVENTION

The invention is directed to systems and methods for increasing stability of dronabinol compositions.

BACKGROUND OF THE INVENTION

Dronabinol is a naturally occurring compound found in *Cannabis saliva L.*, having the following chemical structure:

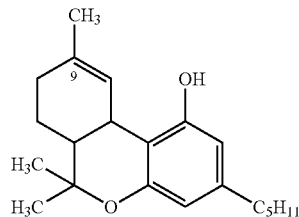

(6aR-trans)-6a,7,8,10a-tetrahyrdo-6,6,9-trimethyl-3-pentyl-6H-dibenzo[b,d]pyran-1-ol Dronabinol, also known as delta-9-tetrahydrocannabinol or $\Delta^9$-THC, has found its place in recent years in a synthetically produced form as an approved therapy for various conditions, such as chemotherapy-induced nausea and vomiting in patients who have failed to respond adequately to conventional anti-emetics.

A currently marketed dronabinol composition is a soft gelatin capsule (dronabinol solution in sesame oil encapsulated in a soft gelatin shell). Dronabinol soft gelatin capsules lack stability at room temperature, and therefore must be stored in a cool environment between 8° C. and 15° C. or refrigerated.

There remains a need in the art for a dronabinol oral solid dosage form which is stable for extended periods of time at room temperature.

All references cited herein are incorporated by reference in their entireties for all purposes.

OBJECTS AND SUMMARY

It is an object of certain embodiments of the present invention to provide systems and methods for increasing the stability of dronabinol compositions.

It is an object of certain embodiments of the present invention to provide systems and methods for increasing the stability of dronabinol compositions at room temperature for extended periods of time.

It is another object of certain embodiments of the present invention to provide systems and methods for increasing the shelf life of dronabinol compositions.

In certain embodiments, the present invention is directed to a packaging system comprising: a container housing (i) a dronabinol oral solid dosage form; and (ii) an oxygen scavenger.

In certain embodiments, the present invention is directed to a method of packaging a dronabinol oral solid dosage form comprising: placing into a container (i) the dronabinol oral solid dosage form and (ii) an oxygen scavenger.

In certain embodiments, the present invention is directed to a method of increasing the stability of a dronabinol oral solid dosage form comprising: placing into a container (i) the dronabinol oral solid dosage form and (ii) an oxygen scavenger.

In certain embodiments, the present invention is directed to a method of retarding or preventing oxidative degradation of a dronabinol oral solid dosage form comprising: placing into a container (i) the dronabinol oral solid dosage form, and (ii) an oxygen scavenger.

In certain embodiments, the oxygen scavenger placed into the container is contained in a canister or packet.

In describing the present invention, the following terms are to be used as indicated below. As used herein, the singular forms "a," "an," and "the" include plural references unless the context clearly indicates otherwise. Thus, for example, reference to "an oxygen scavenger" includes a single oxygen scavenger as well as a mixture of two or more different oxygen scavengers.

The terms "packet" and "sachet" are used herein interchangeably.

The term "oxygen scavenger(s)" or "oxygen scavenging" is used herein in a broad sense and refers to any material or compound that can react with oxygen to change the oxidation state including, e.g., antioxidants, and any mixture or combinations thereof. It should be noted that in a preferred embodiment dronabinol itself is not an oxygen scavenger in the context of the present invention.

The term "antioxidant" as used herein refers to an enzyme or other organic molecule that can react with oxygen.

As used herein, the terms "dronabinol" and "$\Delta^9$-THC" are used interchangeably and refer to trans-(−)-$\Delta^9$-THC, trans-(+)-$\Delta^9$-THC, (±)-$\Delta^9$-THC, or any mixture thereof.

The term "cannabanoids" refers to $\Delta^9$-THC including trans-$\Delta^9$-THC and cis-$\Delta^9$-THC; structural isomers of $\Delta^9$-THC having a molecular formula $C_{21}H_{30}O_2$, including $\Delta^8$-THC, (−)-iso-$\Delta^8$-THC, and (+)-iso-$\Delta^8$-THC, cannabinol and structural isomers of cannabinol having a molecular formula of $C_{21}H_{28}O_2$, $\Delta^9$-THC-carboxylic acid; $\Delta^9$-THC precursors including cannabidiol (CBD), abn-CBD, (+)-abn-CBD, olivetol, (+)-p-mentha-2,8-dien-1-ol and (−)-p-mentha-2,8-dien-1-ol; salts thereof, and derivatives thereof including acids, ethers, esters, amines and the like, as described, e.g., in U.S. Patent Application Publication No. 2009/0298930.

The term "cis" refers to the stereoisomerism about a carbon-carbon double bond, a monocyclic ring, a fused bicyclic ring, or a bridged bicyclic ring wherein the highest ranking substituent on each of the two carbons of relevance are on the same side, which substituent ranking is based on the sequence rules of the Cahn-Ingold-Prelog system.

The term "trans" refers to the stereoisomerism about a carbon-carbon double bond, a monocyclic ring, a fused bicyclic ring, or a bridged bicyclic ring wherein the highest ranking substituent on each of the two carbons of relevance are on opposite sides, which substituent ranking is based on the sequence rules of the Cahn-Ingold-Prelog system.

The term "stable" or "stability" as used herein with respect to dronabinol refers to a dronabinol oral solid dosage form having less than 1% impurities when measured at a particular time point under specified conditions. For example, a room-temperature dronabinol oral solid dosage form is considered to be stable when it contains less than 1% impurities when measured at a specified time (e.g., 3 months) after storage conditions at 25° C. and 60% relative humidity. Preferred stable dronabinol oral solid dosage forms have less than 0.5% impurities or even more preferable less than 0.35% impurities when measured under specific conditions and at a particular time point.

Impurities of the dronabinol oral dosage form that are measured at a particular time point are typically Deg a, Deg b, Deg c, Deg d, Deg e, Deg f, Deg g, Cannabinol, Deg x, and Deg h. If present, any other unknown individual impurities may also be measured and contribute to the impurities of the dronabinol oral dosage form.

The term "oral solid dosage forms" as used herein includes the following dosage forms: tablets, pills, pellets, multi-particulates, capsules, capsules containing liquid (such as liquid-filled soft gelatin capsules), capsules containing powders, capsules containing multi-particulates, lozenges, or any other form suitable for oral use.

DETAILED DESCRIPTION

Oxidative degradation is one of the major issues for dronabinol compositions. To avoid oxidative degradation, oral dronabinol compositions typically require storage under low temperatures, preferably under refrigeration. However, the need for refrigeration can be burdensome on vendors who warehouse and ship the drug, as they cannot store the compositions under standard warehouse conditions. In addition to special storage requirements, the compositions are also required to be refrigerated during shipping, causing a further burden that vendors need to address. The storage problem extends to the patient, who also must keep the medication cold at home and while traveling.

In attempts to address this issue, it has been suggested that oxygen scavengers be incorporated directly into the dronabinol compositions. However, this method is not without drawbacks, as it calls for the addition of a further compound to the composition, which can add to unwanted side effects of the medication.

By virtue of the present invention, there is provided dronabinol formulations with increased shelf life by packaging the dronabinol in a container with an oxygen scavenger. Thus, there is no need to alter the composition. Instead, according to the present invention, the oral solid dosage form is packaged in a container along with a separate oxygen scavenger, which acts to reduce or prevent oxidative degradation and increase shelf life of the composition.

Oxygen Scavenging Materials

Oxygen scavenging materials used in accordance with the present invention may comprise oxygen scavenging substances. Suitable oxygen-scavenging substances comprise at least one material capable of reacting with or absorbing molecular oxygen, thereby limiting the amount of oxygen available for oxidative degradation. Preferably, materials are selected that do not react with oxygen so quickly that handling of the materials is impracticable. Therefore, stable oxygen-scavenging materials that do not readily explode or burn upon contact with molecular oxygen and are useful during extended shelf-life are preferred.

Oxygen scavengers that can be utilized in the present invention include those based on metal (e.g., organometallic ligands, iron, calcium, magnesium, scandium, titanium, vanadium, chromium, manganese, cobalt, nickel, copper, zinc, silver, tin, aluminum, antimony, germanium, silicon, lead, cadmium, rhodium or combinations thereof), sulfites, boron, glycols and sugar alcohols (e.g., catechol), oxidative enzymes (e.g., glucose oxidase), antioxidants (e.g., ascorbic acid), unsaturated fatty acids and hydrocarbons, palladium catalysts, yeast, photosensitive dyes, polyamides (e.g., polydiene block copolymers or polymer bound olefins), aromatic nylon, or any mixtures thereof.

The term "organic based scavenger" as used herein includes the following oxygen scavengers glycols, sugar alcohols (e.g. catechol), ascorbic acid, unsaturated fatty acids, hydrocarbons, photosensitive dyes or combinations thereof.

The term "non-organic based scavenger" as used herein includes the following oxygen scavengers based on metal (e.g., organometallic ligands, iron, calcium, magnesium, scandium, titanium, vanadium, chromium, manganese, cobalt, nickel, copper, zinc, silver, tin, aluminum, antimony, germanium, silicon, lead, cadmium, rhodium or combinations thereof), sulfites, boron, palladium catalysts, and combinations thereof.

The term "polymer based scavenger" as used herein includes the following oxygen scavengers polyamides (e.g., polydiene block copolymers or polymer bound olefins), aromatic nylon, and combinations thereof.

The term "enzym based scavenger" as used herein includes the following oxygen scavengers oxidative enzymes such as oxidases, e.g. glucose oxidase, yeast, or combinations thereof.

The term "oxidative degradation" as used herein refers to the oxidation of the dronabinol to other components such as the degradation products listed above as impurities.

Also contemplated by the present invention are containers that may comprise at least two or more oxygen scavenging materials, wherein each material has different oxygen scavenging properties.

The oxygen scavenging materials may be contained in a canister or packet/sachet that is placed into the contained which houses the dronabinol composition. In other embodiments, the oxygen scavenging materials may also be incorporated into the container which houses the dronabinol composition. For example, containers may be manufactured to contain the oxygen scavenging material within the container itself, as can be found in, e.g., Oxy-Guard® Barrier Bottles (available from Süd-Chemie AG), extrusion blow-molded six-layer pharmaceutical containers which incorporate oxygen scavenging materials within at least one of the six layers to provide against oxidation of the contents.

Commercially available oxygen scavenger materials include, e.g., FreshPax® sachets (available from Multisorb Technologies Inc), Ageless® Z (Ageless-Z is designated as Z-100, Z-1000, etc., to indicate the milliliters of oxygen with which a single packet will react), StabilOx® (available from Multisorb Technologies Inc), O-Busters® (available from Hsiao Sung Non-Oxygen Chemical Co., Ltd), Bioka Oxygen Absorber (available from Bioka Ltd.), PharmaKeep® (Types CH, KH and KD) and the like.

Dronabinol Compositions

The dronabinol compositions of the present invention comprise trans-(−)-$\Delta^9$-THC, trans-(+)-$\Delta^9$-THC, or (±)-$\Delta^9$-THC. In certain embodiments, the dronabinol compositions of the present invention comprise at least about 98%, at least about 99%, at least about 99.5%, at least 99.8%, at least 99.9%, or at least 99.95% by weight of trans-(−)-$\Delta^9$-THC based on the total amount of cannabinoids in the composition. In other embodiments, the dronabinol compositions of the present invention comprise at least about 98%, at least about 99%, at least about 99.5%, at least about 99.8%, at least 99.9%, or at least 99.95% by weight of trans-(+)-$\Delta^9$-THC based on the total amount of cannabinoids in the composition. In other embodiments, the dronabinol compositions of the present invention comprise less than about 0.05% by weight of $\Delta^9$-tetrahydrocannabinol acid based on the total amount of cannabinoids in the composition.

In certain embodiments, the dronabinol oral solid dosage forms contain about 2.5 mg, about 5 mg, or about 10 mg of $\Delta^9$-THC.

The dronabinol compositions of the present invention are oral solid dosage forms, in the form of, e.g., tablets, pills, pellets, multi-particulates, capsules, capsules containing liquid, capsules containing powders, capsules containing multi-particulates, lozenges, or any other form suitable for use. Most preferably, the dronabinol compositions are in the form of a gelatin capsule, and even more preferably in the form of a soft gelatin capsule (e.g., Marinol® (dronabinol) capsules). Techniques and compositions for making oral solid dosage forms are described in Pharmaceutical Dosage Forms: Tablets (Lieberman, Lachman and Schwartz, eds., 2nd ed.) published by Marcel Dekker, Inc. Techniques and compositions for making tablets (compressed and molded), capsules (hard and soft gelatin) and pills are also described in Remington's Pharmaceutical Sciences 1553-1593 (Arthur Osol, ed., $16^{th}$ ed., Mack Publishing, Easton, Pa. 1980).

The dronabinol compositions useful in the present invention comprise a suitable amount of a pharmaceutically acceptable excipient so as to provide the form for proper administration to the patient. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The dronabinol compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, American Pharmaceutical Association (1986).

One or more additional agents may also be included in the dronabinol compositions, such as, e.g., sweetening agents such as fructose, aspartame or saccharin, flavoring agents such as peppermint, oil of wintergreen, or cherry, and coloring agents, to provide palatable dosage forms; as well as preserving agents or stabilizers, to further improve stability.

While the dronabinol oral solid dosage form may itself also contain an oxygen scavenging material, in certain embodiments, the dronabinol oral solid dosage form does not contain its own oxygen scavenger.

In certain embodiments, the dronabinol composition useful in the present invention can be delivered in an immediate release form. In other embodiments, the dronabinol composition useful in the present invention can be delivered in a controlled-release system or sustained-release system. Controlled- or sustained-release pharmaceutical compositions can have a common goal of improving drug therapy over the results achieved by their non-controlled or non-sustained-release counterparts. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the dronabinol, and can thus improve efficacy and/or reduce the occurrence of adverse side effects.

Controlled- or sustained-release compositions can immediately release an amount of the dronabinol upon administration that promptly produces the desired therapeutic or prophylactic effect, and gradually and continually release additional amounts of the dronabinol to maintain a level of therapeutic or prophylactic effect over an extended period of time. To maintain a constant level of the dronabinol in the body, the pharmaceutical oral solid dosage form can release the active from the dosage form at a rate that will replace the amount of active being metabolized and excreted from the body. Controlled- or sustained-release of an active ingredient can be triggered by any one or more of various conditions, including but not limited to, a change in pH, a change in temperature, concentration or availability of enzymes, or a change in the availability of water.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of the active ingredient using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release compositions known in the art can be readily selected for use with the active ingredient of the invention in view of this disclosure. See also Goodson, "Dental Applications" (pp. 115-138) in Medical Applications of Controlled Release, Vol. 2, Applications and Evaluation, R. S. Langer and D. L. Wise eds., CRC Press (1984). Other controlled- or sustained-release systems that are discussed in the review by Langer, Science 249:1527-1533 (1990) can be selected for use according to the present invention. In one embodiment, a pump can be used (Langer, Science 249:1527-1533 (1990); Sefton, CRC Crit. Ref Biomed. Eng. 14:201 (1987); Buchwald et al., Surgery 88:507 (1980); and Saudek et al., N. Engl. J. Med. 321:574 (1989)). In another embodiment, polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, J. Macromol. Sci. Rev. Macromol. Chem. 23:61 (1983); Levy et al., Science 228: 190 (1985); During et al., Ann. Neurol. 25:351 (1989); and Howard et al., J. Neurosurg. 71:105 (1989)).

The dronabinol oral solid dosage form useful in the present invention can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release compositions. A time-delay material such as glycerol monostearate or glycerol stearate can also be used. Standard excipients can be included, such as mannitol, lactose, starch, magnesium stearate, sodium saccharin, cellulose, and magnesium carbonate. In one embodiment, the excipients are of pharmaceutical grade.

Packaging Systems

In accordance with the present invention, the dronabinol oral solid dosage form is placed into a container, along with an oxygen-scavenging material. In certain embodiments, a moisture absorber is also added to the container. The moisture absorber can be added as a separate component, or may be incorporated with the oxygen scavenging material. In certain embodiments, the moisture absorber can be a desiccant.

Containers used in the present invention can be any packaging container suitable to house pharmaceutical formulations. Examples of containers which may be used in the present invention include, e.g., bottles, vials, blister packs, foil packs, pouches, bulk containers, single dose containers, multidose containers and the like. The containers may be made, e.g., of plastic or glass, and may be clear, colored, tinted, coated, etc. In certain embodiments, the containers are made with high density polyethylene (HDPE), which provides a moisture barrier to the contents.

Containers used in the present invention may be used in conjunction with any suitable type of closure known in the art, such as, e.g., rubber closures, screw caps, crown caps, snap-on closures, friction-fit closures, tamper evident seals, dispensing closures, child-resistant closures, and any combination thereof. In certain embodiments, the closure will prevent any excess oxygen from entering the container when secured onto the container.

Preferably, the packaging system of the present invention provides stability of the dronabinol oral solid dosage form at room temperature for at least 3 months, at least 6 months, at least 12 months, at least 18 months, at least 24 months, at least 30 months, or at least 36 months.

Preferably, the packaging system of the present invention provides a room temperature stable dronabinol oral solid dosage form when measured at 3 months, at 6 months, at 12 months, at 18 months, at 24 months, at 30 months, or at 36 months.

The dronabinol oral solid dosage form packaged with the oxygen-scavenging material preferably provides less than 1%, less than 0.9%, less than 0.8%, less than 0.7%, less than 0.6%, less than 0.5%, less than 0.4%, less than 0.35%, less than 0.3%, less than 0.2% or less than 0.1% impurities of the dronabinol when measured at 3 months, at 6 months, at 12 months, at 18 months, at 24 months, at 30 months, or at 36 months after storage conditions of 40° C. and 75% relative humidity.

The dronabinol oral solid dosage form packaged with the oxygen-scavenging material preferably provides less than 1%, less than 0.9%, less than 0.8%, less than 0.7%, less than 0.6%, less than 0.5%, less than 0.4%, less than 0.35%, less than 0.3%, less than 0.2% or less than 0.1% impurities of the dronabinol when measured at 3 months, at 6 months, at 12 months, at 18 months, at 24 months, at 30 months, or at 36 months after storage conditions of 40° C. and 75% relative humidity as compared to a control formulation (without an oxygen scavenger material added to the container).

The dronabinol oral solid dosage form packaged with the oxygen-scavenging material preferably provides less than 1%, less than 0.9%, less than 0.8%, less than 0.7%, less than 0.6%, less than 0.5%, less than 0.4%, less than 0.35%, less than 0.3%, less than 0.2% or less than 0.1% impurities of the dronabinol when measured at 3 months, at 6 months, at 12 months, at 18 months, at 24 months, at 30 months, or at 36 months after storage conditions of 25° C. and 60% relative humidity.

The dronabinol oral solid dosage form packaged with the oxygen-scavenging material preferably provides less than 1%, less than 0.9%, less than 0.8%, less than 0.7%, less than 0.6%, less than 0.5%, less than 0.4%, less than 0.35%, less than 0.3%, less than 0.2% or less than 0.1% impurities of the dronabinol when measured at 3 months, at 6 months, at 12 months, at 18 months, at 24 months, at 30 months, or at 36 months after storage conditions of 25° C. and 60% relative humidity as compared to a control formulation (without an oxygen scavenger material added to the container).

EXAMPLES

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in composition or minor changes in experimental design, are to be considered to fall within the scope of the invention incorporated herein.

Example 1

10 mg dronabinol softgel capsules (dronabinol solution in sesame oil 10% w/w)(Pharmaceutics International, Inc.) were placed into bottles. A StabilOx® DF-100-H31 canister (Multisorb Technologies) was added to each bottle. The stability of the capsules was tested at three months after storage under refrigerated conditions (2° C.-8° C.). The stability, as determined from assay and chromatographic purity was determined. Results are shown in Table 1 below.

TABLE 1

| Testing Conditions | Components | Specifications and Limits | Results |
|---|---|---|---|
| 2° C.-8° C. | % Label Claim | 90.0%-110.0% | 102.7 |
| | Deg a (RRT 0.30) | NMT 0.2% | <0.10 |
| | Deg b (RRT 0.35) | NMT 0.2% | Not detected |
| | Deg c (RRT 0.38) | NMT 0.2% | Not detected |
| | Deg d (RRT 0.40) | NMT 0.1% | Not detected |
| | Deg e (RRT 0.48) | NMT 0.2% | Not detected |
| | Deg f (RRT 0.50) | NMT 0.4% | 0.11 |
| | Deg g (RRT 0.60) | NMT 0.1% | Not detected |
| | Cannabinol (RRT 0.78) | NMT 0.2% | Not detected |
| | Deg x (RRT 0.85) | NMT 0.3% | <0.10 |
| | Deg h (RRT 0.96) | NMT 0.5% | <0.10 |
| | Any other individual unknown impurities | NMT 0.2% | None detected |
| | Total related impurities | NMT 2.0% | 0.1 |

NMT: not more than
RRT: relative retention time

Example 2

10 mg dronabinol softgel capsules (dronabinol solution in sesame oil 10% w/w) (Pharmaceutics International, Inc.) were placed into bottles. A StabilOx® DF-100-H31 canister (Multisorb Technologies) was added to each bottle. The stability of the capsules was tested at three months after under accelerated conditions (i.e., 40° C./75% RH). The stability, as determined from assay and chromatographic purity was determined. Results are shown in Table 2 below.

TABLE 2

| Testing Conditions | Components | Specifications and Limits | Results |
|---|---|---|---|
| 40° C./75% RH | % Label Claim | 90.0%-110.0% | 102.2 |
| | Deg a (RRT 0.30) | NMT 0.2% | <0.10 |
| | Deg b (RRT 0.35) | NMT 0.2% | <0.10 |
| | Deg c (RRT 0.38) | NMT 0.2% | Not detected |
| | Deg d (RRT 0.40) | NMT 0.1% | Not detected |
| | Deg e (RRT 0.48) | NMT 0.2% | Not detected |
| | Deg f (RRT 0.50) | NMT 0.4% | <0.10 |
| | Deg g (RRT 0.60) | NMT 0.1% | Not detected |
| | Cannabinol (RRT 0.78) | NMT 0.2% | Not detected |
| | Deg x (RRT 0.85) | NMT 0.3% | 0.14 |
| | Deg h (RRT 0.96) | NMT 0.5% | 0.21 |
| | Any other individual unknown impurities | NMT 0.2% | None detected |
| | Total related impurities | NMT 2.0% | 0.4 |

NMT: not more than
RRT: relative retention time

Example 3

10 mg dronabinol softgel capsules (dronabinol solution in sesame oil 10% w/w)(Pharmaceutics International, Inc.) were placed into bottles. A StabilOx® DF-100-H31 canister (Multisorb Technologies) was added to each bottle. The stability of the capsules was tested at three months after storage under room temperature conditions (25° C./60% RH). The stability, as determined from assay and chromatographic purity was determined. Results are shown in Table 3 below.

TABLE 3

| Testing Conditions | Components | Specifications and Limits | Results |
|---|---|---|---|
| 25° C./60% RH | % Label Claim | 90.0%-110.0% | 104.6 |
| | Deg a (RRT 0.30) | NMT 0.2% | <0.10 |
| | Deg b (RRT 0.35) | NMT 0.2% | <0.10 |
| | Deg c (RRT 0.38) | NMT 0.2% | <0.10 |
| | Deg d (RRT 0.40) | NMT 0.1% | Not detected |
| | Deg e (RRT 0.48) | NMT 0.2% | Not detected |
| | Deg f (RRT 0.50) | NMT 0.4% | 0.12 |
| | Deg g (RRT 0.60) | NMT 0.1% | Not detected |
| | Cannabinol (RRT 0.78) | NMT 0.2% | Not detected |
| | Deg x (RRT 0.85) | NMT 0.3% | 0.11 |
| | Deg h (RRT 0.96) | NMT 0.5% | 0.21 |
| | Any other individual unknown impurities | NMT 0.2% | None detected |
| | Total related impurities | NMT 2.0% | 0.3 |

NMT: not more than
RRT: relative retention time

Example 4

5 mg dronabinol softgel capsules (dronabinol solution in sesame oil 10% w/w)(Pharmaceutics International, Inc.) were placed into bottles. A StabilOx® DF-100-H31 canister (Multisorb Technologies) was added to each bottle. The stability of the capsules was tested at three months after storage under refrigerated conditions (2° C.-8° C.). The stability, as determined from assay and chromatographic purity was determined. Results are shown in Table 4 below.

TABLE 4

| Testing Conditions | Components | Specifications and Limits | Results |
|---|---|---|---|
| 2° C.-8° C. | % Label Claim | 90.0%-110.0% | 101.4 |
| | Deg a (RRT 0.30) | NMT 0.2% | Not detected |
| | Deg b (RRT 0.35) | NMT 0.2% | Not detected |
| | Deg c (RRT 0.38) | NMT 0.2% | Not detected |
| | Deg d (RRT 0.40) | NMT 0.1% | Not detected |
| | Deg e (RRT 0.48) | NMT 0.2% | Not detected |
| | Deg f (RRT 0.50) | NMT 0.4% | 0.11 |
| | Deg g (RRT 0.60) | NMT 0.1% | Not detected |
| | Cannabinol (RRT 0.78) | NMT 0.2% | Not detected |
| | Deg x (RRT 0.85) | NMT 0.3% | <0.10 |
| | Deg h (RRT 0.96) | NMT 0.5% | <0.10 |
| | Any other individual unknown impurities | NMT 0.2% | None detected |
| | Total related impurities | NMT 2.0% | 0.1 |

NMT: not more than
RRT: relative retention time

Example 5

5 mg dronabinol softgel capsules (dronabinol solution in sesame oil 10% w/w) (Pharmaceutics International, Inc.) were placed into bottles. A StabilOx® DF-100-H31 canister (Multisorb Technologies) was added to each bottle. The stability of the capsules was tested at three months after storage under accelerated conditions (i.e., 40° C./75% RH). The stability, as determined from assay and chromatographic purity was determined. Results are shown in Table 5 below.

TABLE 5

| Testing Conditions | Components | Specifications and Limits | Results |
|---|---|---|---|
| 40° C./75% RH | % Label Claim | 90.0%-110.0% | 100.7 |
| | Deg a (RRT 0.30) | NMT 0.2% | Not detected |
| | Deg b (RRT 0.35) | NMT 0.2% | <0.10 |
| | Deg c (RRT 0.38) | NMT 0.2% | Not detected |
| | Deg d (RRT 0.40) | NMT 0.1% | Not detected |
| | Deg e (RRT 0.48) | NMT 0.2% | Not detected |
| | Deg f (RRT 0.50) | NMT 0.4% | <0.10 |
| | Deg g (RRT 0.60) | NMT 0.1% | Not detected |
| | Cannabinol (RRT 0.78 | NMT 0.2% | Not detected |
| | Deg x (RRT 0.85) | NMT 0.3% | 0.17 |
| | Deg h (RRT 0.96) | NMT 0.5% | 0.21 |
| | Any other individual unknown impurities | NMT 0.2% | None detected |
| | Total related impurities | NMT 2.0% | 0.4 |

NMT: not more than
RRT: relative retention time

Example 6

5 mg dronabinol softgel capsules (dronabinol solution in sesame oil 10% w/w)(Pharmaceutics International, Inc.) were placed into bottles. A StabilOx® DF-100-H31 canister (Multisorb Technologies) was added to each bottle. The stability of the capsules was tested at three months after storage under room temperature conditions (25° C./60% RH). The stability, as determined from assay and chromatographic purity was determined. Results are shown in Table 6 below.

TABLE 6

| Testing Conditions | Components | Specifications and Limits | Results |
|---|---|---|---|
| 25° C./60% RH | % Label Claim | 90.0%-110.0% | 100.9 |
| | Deg a (RRT 0.30) | NMT 0.2% | Not detected |
| | Deg b (RRT 0.35) | NMT 0.2% | <0.10 |
| | Deg c (RRT 0.38) | NMT 0.2% | Not detected |
| | Deg d (RRT 0.40) | NMT 0.1% | Not detected |
| | Deg e (RRT 0.48) | NMT 0.2% | Not detected |
| | Deg f (RRT 0.50) | NMT 0.4% | 0.10 |
| | Deg g (RRT 0.60) | NMT 0.1% | Not detected |
| | Cannabinol (RRT 0.78) | NMT 0.2% | Not detected |
| | Deg x (RRT 0.85) | NMT 0.3% | <0.10 |
| | Deg h (RRT 0.96) | NMT 0.5% | 0.13 |
| | Any other individual unknown impurities | NMT 0.2% | None detected |
| | Total related impurities | NMT 2.0% | 0.2 |

NMT: not more than
RRT: relative retention time

Example 7

2.5 mg dronabinol softgel capsules (dronabinol solution in sesame oil 10% w/w)(Pharmaceutics International, Inc.) were placed into bottles. A StabilOx® DF-100-H31 canister (Multisorb Technologies) was added to each bottle. The stability of the capsules was tested initially after manufacturing and then again at three months after storage under refrigerated conditions (2° C.-8° C.). A control was used for comparison, having the same dronabinol formulation packaged without the StabilOx® canister. The stability, as determined from assay and chromatographic purity was determined. Results are shown in Table 7 below.

TABLE 7

| Testing Conditions | Components | Specifications and Limits | Results (INITIAL) | Results (3 MONTHS) | Results (CONTROL) |
|---|---|---|---|---|---|
| 2° C.-8° C. | % Label Claim | 90.0%-110.0% | 101.9 | 102.3 | 99.3 |
| | Deg a (RRT 0.30) | NMT 0.2% | <0.10 | <0.10 | <0.10 |
| | Deg b (RRT 0.35) | NMT 0.2% | Not detected | <0.10 | Not detected |
| | Deg c (RRT 0.38) | NMT 0.2% | <0.10 | Not detected | Not detected |
| | Deg d (RRT 0.40) | NMT 0.1% | Not detected | Not detected | Not detected |
| | Deg e (RRT 0.48) | NMT 0.2% | Not detected | Not detected | Not detected |
| | Deg f (RRT 0.50) | NMT 0.4% | 0.10 | 0.11 | 0.10 |
| | Deg g (RRT 0.60) | NMT 0.1% | Not detected | Not detected | Not detected |
| | Cannabinol (RRT 0.78) | NMT 0.2% | Not detected | Not detected | Not detected |
| | Deg x (RRT 0.85) | NMT 0.3% | <0.10 | <0.10 | Not detected |
| | Deg h (RRT 0.96) | NMT 0.5% | <0.10 | Not detected | 0.10 |
| | Any other individual unknown impurities | NMT 0.2% | None detected | None detected | None detected |
| | Total related impurities | NMT 2.0% | 0.1 | 0.1 | 0.1 |

NMT: not more than
RRT: relative retention time

Example 8

2.5 mg dronabinol softgel capsules (dronabinol solution in sesame oil 10% w/w) (Pharmaceutics International, Inc.) were placed into bottles. A StabilOx® DF-100-H31 canister (Multisorb Technologies) was added to each bottle. A Control was used for comparison, having the same dronabinol formulation packaged without the StabilOx® canister. The stability of the capsules was tested initially after manufacture and at three months after storage under accelerated conditions (i.e., 40° C./75% RH). The stability, as determined from assay and chromatographic purity was determined. Results are shown in Table 8 below.

TABLE 8

| Testing Conditions | Components | Specifications and Limits | Results (INITIAL) | Results (3 MONTHS) | Results (CONTROL) |
|---|---|---|---|---|---|
| 40° C./75% RH | % Label Claim | 90.0%-110.0% | 102.2 | 98.5 | 97.8 |
| | Deg a (RRT 0.30) | NMT 0.2% | <0.10 | <0.10 | 0.13 |

TABLE 8-continued

| Testing Conditions | Components | Specifications and Limits | Results (INITIAL) | Results (3 MONTHS) | Results (CONTROL) |
|---|---|---|---|---|---|
| | Deg b (RRT 0.35) | NMT 0.2% | Not detected | <0.10 | 0.17 |
| | Deg c (RRT 0.38) | NMT 0.2% | Not detected | Not detected | <0.10 |
| | Deg d (RRT 0.40) | NMT 0.1% | Not detected | Not detected | Not detected |
| | Deg e (RRT 0.48) | NMT 0.2% | Not detected | Not detected | Not detected |
| | Deg f (RRT 0.50) | NMT 0.4% | <0.10 | <0.10 | 0.20 |
| | Deg g (RRT 0.60) | NMT 0.1% | Not detected | Not detected | Not detected |
| | Cannabinol (RRT 0.78 | NMT 0.2% | Not detected | Not detected | Not detected |
| | Deg x (RRT 0.85) | NMT 0.3% | Not detected | 0.20 | 0.53** |
| | Deg h (RRT 0.96) | NMT 0.5% | Not detected | 0.16 | 0.48 |
| | Any other individual unknown impurities | NMT 0.2% | None detected | None detected | <0.10 |
| | Total related impurities | NMT 2.0% | 0.10 | 0.4 | 1.5 |

NMT: not more than
RRT: relative retention time

Example 9

2.5 mg dronabinol softgel capsules (dronabinol solution in sesame oil 10% w/w)(Pharmaceutics International, Inc.) were placed into bottles. A StabilOx® DF-100-H31 canister (Multisorb Technologies) was added to each bottle. A Control was used for comparison, having the same dronabinol formulation packaged without the StabilOx® canister. The stability of the capsules was tested after initial manufacture and again at three months after storage under room temperature conditions (25° C./60% RH). The stability, as determined from assay and chromatographic purity was determined. Results are shown in Table 9 below.

TABLE 9

| Testing Conditions | Components | Specifications and Limits | Results (INITIAL) | Results (3 MONTHS) | Results (CONTROL) |
|---|---|---|---|---|---|
| 25° C./60% RH | % Label Claim | 90.0%-110.0% | 101.9 | 102.4 | 98.8 |
| | Deg a (RRT 0.30) | NMT 0.2% | <0.10 | <0.10 | <0.10 |
| | Deg b (RRT 0.35) | NMT 0.2% | Not detected | <0.10 | <0.10 |
| | Deg c (RRT 0.38) | NMT 0.2% | <0.10 | Not detected | Not detected |
| | Deg d (RRT 0.40) | NMT 0.1% | Not detected | Not detected | Not detected |
| | Deg e (RRT 0.48) | NMT 0.2% | Not detected | Not detected | Not detected |
| | Deg f (RRT 0.50) | NMT 0.4% | 0.10 | 0.11 | 0.13 |
| | Deg g (RRT 0.60) | NMT 0.1% | Not detected | Not detected | Not detected |
| | Cannabinol (RRT 0.78) | NMT 0.2% | Not detected | Not detected | Not detected |
| | Deg x (RRT 0.85) | NMT 0.3% | <0.10 | 0.11 | 0.13 |
| | Deg h (RRT 0.96) | NMT 0.5% | <0.10 | 0.12 | 0.15 |
| | Any other individual unknown impurities | NMT 0.2% | None detected | None detected | Not detected |
| | Total related impurities | NMT 2.0% | 0.10 | 0.3 | 0.4 |

NMT: not more than
RRT: relative retention time

What is claimed:

1. A packaging system comprising a plastic or glass container housing:

(i) at least one soft gelatin capsule comprising dronabinol and an oxygen scavenger; and (ii) a separate iron-based oxygen scavenger that does not comprise silicon, wherein the system provides not more than 0.3% by weight of degradant×(Relative Retention Time 0.85) of dronabinol when measured at 3 months after storage under conditions of 40° C. and 75% relative humidity.

2. The packaging system of claim 1, wherein the separate iron-based oxygen scavenger is contained in a canister or packet.

3. The packaging system of claim 1, wherein the separate iron-based oxygen scavenger is incorporated into integral components of the container.

4. A method of packaging a dronabinol oral solid dosage form comprising placing into a plastic or glass container:
  (i) at least one soft gelatin capsule comprising dronabinol and an oxygen scavenger; and
  (ii) a separate iron-based oxygen scavenger that does not comprise silicon,
  wherein the system provides not more than 0.3% by weight of degradant×(Relative Retention Time 0.85) of dronabinol when measured at 3 months after storage under conditions of 40° C. and 75% relative humidity.

5. The method of claim 4, wherein the separate iron-based oxygen scavenger is contained in a canister or packet.

6. The method of claim 4, wherein the separate iron-based oxygen scavenger is incorporated into integral components of the container.

7. The method of claim 4, wherein the oxygen scavenger in the at least one soft gelatin capsule is selected from the group consisting of organic-based scavengers, non-organic-based scavengers, polymer-based scavengers, enzyme-based scavengers and mixtures thereof.

8. A method of increasing stability of a dronabinol oral solid dosage form comprising placing in a plastic or glass container:
  (i) at least one soft gelatin capsule comprising dronabinol and an oxygen scavenger; and
  (ii) a separate iron-based oxygen scavenger that does not comprise silicon,
  wherein the system provides not more than 0.3% by weight of degradant×(Relative Retention Time 0.85) of dronabinol when measured at 3 months after storage under conditions of 40° C. and 75% relative humidity.

9. The method of claim 8, wherein the separate iron-based oxygen scavenger is contained in a canister or packet.

10. The method of claim 8, wherein the separate iron-based oxygen scavenger is incorporated into integral components of the container.

11. The packaging system of claim 1, wherein the packaging system provides stability of the at least one soft gelatin capsule at room temperature for a time period of at least three months.

12. The packaging system of claim 1, wherein the system provides less than 0.5% by weight of impurities of dronabinol when measured at 3 months after storage under conditions of 40° C. and 75% relative humidity.

13. The packaging system of claim 1, wherein the system provides less than 0.35% by weight of impurities of dronabinol when measured at 3 months after storage under conditions of 25° C. and 60% relative humidity.

14. The packaging system of claim 1, wherein the system provides less than 0.2% by weight of impurities of dronabinol when measured at 3 months after storage under conditions of 25° C. and 60% relative humidity.

15. The packaging system of claim 1, wherein the at least one soft gelatin capsule comprises trans-(−)-$\Delta^9$-tetrahydrocannabinol.

16. The packaging system of claim 15, wherein the at least one soft gelatin capsule comprises at least 98% by weight trans-(−)-$\Delta^9$-tetrahydrocannabinol.

17. The packaging system of claim 1, wherein the system provides less than 1.0% by weight of impurities of dronabinol when measured at 3 months after storage under conditions of 40° C. and 75% relative humidity.

18. The packaging system of claim 1, wherein the oxygen scavenger in the at least one soft gelatin capsule comprises sesame oil.

* * * * *